United States Patent
Liu et al.

(10) Patent No.: US 8,093,192 B2
(45) Date of Patent: *Jan. 10, 2012

(54) PERSONAL WASH COMPOSITIONS COMPRISING SPECIFIC BLENDS OF SATURATED (HYDROGENATED) OIL TO UNSATURATED TRIGLYCERIDE OILS

(75) Inventors: Hongjie Liu, Shelton, CT (US); Kavssery Parameswaran Ananthapadmanabhan, Woodbury, CT (US); David John Lang, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 231 days.

This patent is subject to a terminal disclaimer.

(21) Appl. No.: 12/371,050

(22) Filed: Feb. 13, 2009

(65) Prior Publication Data

US 2010/0210500 A1    Aug. 19, 2010

(51) Int. Cl.
*A61K 7/50* (2006.01)
(52) U.S. Cl. ........ 510/130; 510/156; 510/462; 510/463; 424/70.1
(58) Field of Classification Search .......................... None
See application file for complete search history.

(56) References Cited

U.S. PATENT DOCUMENTS

| | | | |
|---|---|---|---|
| 3,723,325 | A | 3/1973 | Parran |
| 4,565,647 | A | 1/1986 | Lienado |
| 5,009,814 | A | 4/1991 | Kelkenberg et al. |
| 5,389,279 | A | 2/1995 | Au et al. |
| 6,395,690 | B1 | 5/2002 | Tsaur |
| 2004/0234467 | A1 | 11/2004 | Ananthapadmanabhan et al. |
| 2004/0234468 | A1 | 11/2004 | Kerschner et al. |
| 2004/0234469 | A1 | 11/2004 | O'Connor et al. |
| 2004/0234558 | A1* | 11/2004 | O'Connor et al. ............ 424/401 |
| 2004/0235691 | A1 | 11/2004 | Pham et al. |
| 2005/0281851 | A1 | 12/2005 | Cap |

FOREIGN PATENT DOCUMENTS

| | | |
|---|---|---|
| EP | 1479365 A1 | 11/2004 |
| EP | 1479378 A1 | 11/2004 |
| WO | WO 2004/017745 A1 | 3/2004 |

* cited by examiner

*Primary Examiner* — Necholus Ogden, Jr.
(74) *Attorney, Agent, or Firm* — Ronald A. Koatz

(57) ABSTRACT

The present invention provides personal wash compositions where blends of triglyceride oils are specifically formulated to provide functional benefits. Specifically when formulated to have specific blend of saturated to unsaturated oils, perfect balance between, on the one hand, spreadability and deposition and, on the other hand, retention of excellent framing, is achieved.

6 Claims, 6 Drawing Sheets

PERSONAL WASH COMPOSITIONS COMPRISING SPECIFIC BLENDS OF SATURATED (HYDROGENATED) OIL TO UNSATURATED TRIGLYCERIDE OILS

FIELD OF THE INVENTION

The present invention relates to surfactant containing personal wash compositions in which triglyceride oils are used to provide functional benefits (e.g., moisturization). More specifically, the invention relates to compositions comprising triglyceride oils which are blends of fully saturated (hydrogenated) to unsaturated liquid triglyceride oil. When there is a critical ratio of fully hydrogenated triglycerides to liquid triglyceride oil, the triglyceride mixture achieves a preferred balance between (1) a rheology ideal for optimum spreadability and deposition (defined by rheology approximating that of petrolatum) and (2) the ability to obtain optimum foam volumes (defined to approximate that of unsaturated liquid triglyceride oils; typically, such liquid triglyceride oils have less defoaming effect than solid crystals, but do not have optimum rheology required for deposition).

BACKGROUND

Personal wash compositions seek to provide consumers with additional skin benefits beyond simple cleansing. One of the principle benefits provided by such compositions is moisturization. Among the many moisturization benefit agents the most commonly used agents for good moisturization are emollient oils such as triglyceride based oils (e.g. vegetable oils) and petroleum based hydrocarbon oils (e.g., mineral oil or petroleum jelly, also known as petrolatum). These emollients are commonly used for their low cost or good occlusive power.

Emollients such as petrolatum and liquid triglycerides can be easily spread and pressed down onto skin to form a thin, hydrophobic film that can retard skin dehydration and alleviate the irritation or lipid/protein damage from surfactants. The emollient oils play this role in body wash products only when a sufficient amount of the emollient can be deposited and retained after rinsing. In this sense, viscous, semi-solid gels (e.g., petroleum) are typically more efficient than liquid triglyceride oils since, because of their rheology, they are more readily deposited and more difficult to rinse off. On the other hand, triglyceride vegetable oils are natural botanics which have milder properties and are less greasy feeling than petroleum sourced oils.

It would thus be desirable to find a triglyceride vegetable oil blend which could be readily pressed down and deposited onto skin (e.g., has rheological characteristics similar to) as easily as petroleum based oil. One way of accomplishing this is to use solid particles or high melting wax to thicken vegetable oil so that it has rheological properties similar to that of, for example, petrolatum. The problem is that the high crystallinity material in structured oils usually also produces lessened foam values, as compared to the similar formulations without high melting material structured oils.

Unexpectedly, applicants have now discovered that, if a specific ratio of fully hydrogenated and non-hydrogenated vegetable oils is used (e.g., in the case of soybean oil, such that iodine number of mixture is above 70, preferably above 80, preferably 81 to about 120), it is possible to simultaneously produce an emollient which has a rheology similar to that of petrolatum (and should deposit more readily), while also maintaining a foam value which is not depressed relative to use of the unsaturated triglyceride oil alone for a perceivable period of time (e.g., has foam value at least 70% as great as unsaturated triglyceride vegetable oil alone when foam value of otherwise identical liquid composition in which triglycerides are used is measured).

More specifically, to enhance the deposition effectiveness of the occlusive oils while still retaining the substantial lather volume generated by foaming surfactants, regular vegetable oils (unsaturated triglyceride oils) are in effect thickened by simply blending those regular triglyceride oils with their corresponding fully hydrogenated oils at the optimal weight ratios. Non-limiting examples of the partially saturated triglyceride oils which can be structured or thickened while retaining good foam using optimal blends of the invention include sunflower oil, castor oil, coconut oil, cottonseed oil, menhaden oil, palm kernel oil, palm oil, peanut oil, soybean oil, rapeseed oil, linseed oil, rice bran oil, pine oil, sesame oil, rice bran oil, all their corresponding hydrogenated counterparts and mixtures thereof.

EP 1,479,365 discloses benefit agent materials structured with crystalline material. U.S. Publication 2004/023569 A1 discloses non-bar compositions comprising crystalline wax structured benefit agent. U.S. 2004/0234467 A1 discloses compositions comprising structured benefit agent for deposition of hydrophilic benefit agent. EP 1,479,378 relates to bars with crystalline wax structured delivery vehicle.

U.S. 2004/0234468, U.S. 2004/0234469 and U.S. 2004/0234558 disclose structured premix to enhance delivery of hydrophobic agent.

WO 2004/017745 discloses mixing non-hydrogenated and hydrogenated oils for dispersed liquid oil or solid particles in fat phase for food compositions.

None of these references disclose specific blends of fully saturated to unsaturated triglycerides which must be within specifically defined ratios to achieve optimum rheology (e.g., for deposition).

U.S. 2005/0281851 to Cap discloses cosmetic products comprising vegetable oil blends and additional fatty acid where blends have iodine value range of 20-80 and no applicable viscosity range specified. There is no disclosure of the critical ratios of the invention. Further, in at least one emollient of the present invention (e.g., for soybean oil blends) the compositions, include triglyceride oil blends with higher iodine value, specifically an iodine value from 81 to 120 that will give the desired oil viscosity (for deposition). Such blend should have viscosity superior for deposition and maintain good foam compared to the vegetable oil blends with iodine value range of 20-80 in Cap reference. Also, as noted, there is no criticality to ratio of blends in Cap.

BRIEF DESCRIPTION OF INVENTION

The present invention relates to personal product composition comprising:
(1) 1 to 40%, preferably 5 to 40%, more preferably 10-30% by wt. of surfactant system selected from the group consisting of anionic, nonionic, cationic, amphoteric/zwitterionic surfactants and mixtures thereof;
(2) 0.1 to 40%, preferably 30% or less, preferably about 5-30% by wt. of a blend of unsaturated (partially or non-hydrogenated) and saturated (hydrogenated) triglyceride oils where the amount of saturated triglyceride is 15% to 35%, preferably 20 to 30% of the blend and unsaturated liquid triglyceride oil comprises 85 to 65%, preferably 80 to 70% of the blend;
wherein when measured over a range of −20 to 100° C., the crystallinity of oil blends as characterized by enthalpy of phase transition, measured in Joule/gram, of the blend is from 30 to 60, and preferably does not exceed 55;

wherein the foam value of the composition comprising the blend is at least 70% of the foam value of the same composition when no oils or liquid triglyceride oil alone is used instead of said blend.

In one emollient (where triglyceride oil is soybean oil), the iodine value of the blend of hydrogenated soybean oil (HSBO) and unsaturated triglyceride oil (SBO) is above 70, preferably above 80, preferably 81 to 120, more preferably 91 to 105. For soybean oil, these are iodine values which correspond to the critical ratios noted (i.e., critical for enhancing balance between deposition and foaming performance).

The use of such blend in liquid surfactant containing personal product compositions allows the triglyceride to be used which has a rheology similar to that of petrolatum (and hence enhance deposition) while simultaneously maintaining good foam value.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
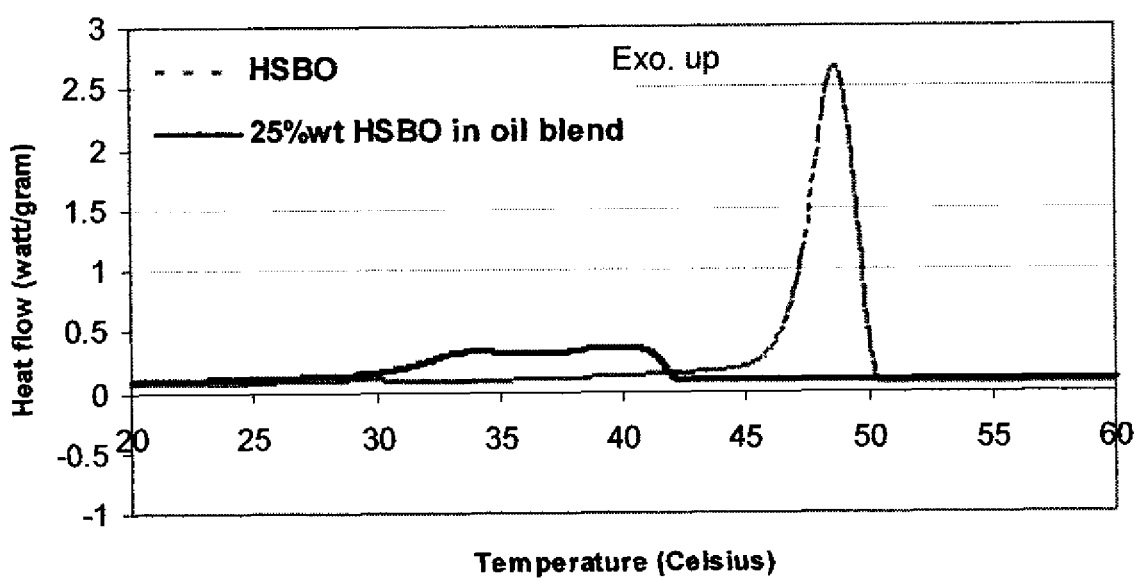
FIG. 1 is DSC (differential scanning calorimetry) diagrams of oil mixture comprising 25 wt % saturated (hydrogenated) soybean oil and 75 wt % unsaturated (liquid) soybean oil compared to a fully hydrogenated oil. The mixture has much lowered and widened phase transition and shifted to lower temperature region which makes it more similar to petrolatum (see FIG. 2).

The present invention relates to surfactant-containing liquid personal wash compositions (preferably aqueous based compositions having >30%, preferably 35% water) comprising specific blends of fully saturated (hydrogenated) to not fully saturated (non or partially hydrogenated) triglyceride oils. Specifically, when a blend is specifically formulated such that the amount of saturated oil is in a defined range, and the amount of unsaturated oil is in a defined range (ranges correspond also to a specific iodine value for the blend), the blend will have precisely the right characteristics such that it will have the optimal shear viscosity and spreadability required to deposit in the superior way petrolatum deposits relative to unsaturated triglyceride (e.g. it will have enough hydrogenated triglyceride, about 20-30%, to increase viscosity of unsaturated triglyceride oils thus deposit analogously to petrolatum, see FIG. 4); and yet the blend will not have so much hydrogenated triglyceride (about 35% preferably no more than 30% upper level that will have flattened thermal phase transition peak over broad range of temperatures, see FIGS. 1 and 2) that it will depress foam value to the point where it is not at least 70% of the foam value of the same composition when no triglyceride oil is used. That is, only blends having about 15-35%, preferably 20-30% of blend fully hydrogenated oil will provide the required rheological and foaming characteristics when used in compositions of the invention.

Specifically, the composition of the invention comprise:

(1) 1% by wt. to 40 wt %, preferably 5 to 40 wt %, more preferably 10 to 35 wt % by wt. of a surfactant selected from the group consisting of anionic surfactant, nonionic surfactant, amphoteric/zwitterionic surfactant, cationic surfactant and mixtures thereof;

(2) 1 to 40% wt., preferably below 30 wt %, preferably 5 to 30 wt % of a blend of saturated (i.e., hydrogenated) and of liquid triglyceride oils (unsaturated), wherein the blend comprises 15 to 35 wt %, preferably 20-30 wt % fully saturated oil and 85 to 65 wt %, preferably 80 to 70 wt % unsaturated oil (e.g., mix of natural unsaturated oil and fully hydrogenated oil to form partially saturated oil).

The blend may be further characterized (1) by an iodine value which corresponds to that specific value for a particular oil; (2) by the phase transition enthalpy of the compositions in which they are used (correlating with the rheology and hence ability to deposit relative to, for example, petrolatum); and (3) by the foam value of the compositions in which the blends are used. The invention is described in greater detail below.

The compositions in which the blends of the invention may be used comprise 1% by wt. to 40% by wt., preferably 5 to 40%, more preferably 10-35% by wt. surfactant. Surfactants may be anionic, nonionic amphoteric/zwitterionic, cationic or mixtures thereof. Examples of the many surfactants which may be used are set forth, for example, in U.S. Pat. No. 6,395,690 to Tsaur.

Anionic may be aliphatic sulfonate (e.g., $C_8$-$C_{22}$ alkane or alkene sulfonate or aromatic sulfonate); alkyl sulfate (including alkyl and alkyl ether sulfate); sulfosuccinate; taurate; sarcosinates; sulfoacetate; alkyl phosphate.

Anionics may also be carboxylates and ether carboxylates. Another preferred class is $C_8$ to $C_{22}$ acyl isethionates. These esters are prepared by reacting alkali metal isethionate with mixed aliphatic fatty acids. In a preferred embodiment, the isethionate surfactant comprises 5 to 25 wt %, preferably 8 to 20 wt % of the composition.

Zwitterionic surfactants are broadly derivates of aliphatic quaternary ammonium, phosphonium and sulfonium compound in which aliphatic radicals are straight or branched chain, and wherein one of the aliphatic substituents contains 8 to 18 carbons and one contains an anionic group, e.g., carboxy, sulfonate, sulfate, phosphate or phosphonate.

Amphoteric surfactants include at least one acid group (e.g., carboxylic or sulphonic acid group). They include quaternary nitrogen and are quaternary amido acid. They typically include $C_7$ to $C_{18}$ alkyl or alkenyl group. Examples include betaines, amido betaines, sulphobetaines.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference. Preferred alkyl polysaccharides are alkylpolyglycosides.

Cationic surfactants are selected from the group consisting of: alkyl trimonnium chloride and methosulfate, and dialkyldimonnium chloride and methyl sulphate, and alkyl alkonium chloride and methyl sulphate and mixtures thereof. These surfactants contain $C_{12}$ to $C_{24}$ carbon atoms per alkyl chain. The most preferred cationic is selected from the group consisting of stearylalkonium chloride, stearyltrimonium chloride. Di-stearyl-dimonium chloride, and mixtures thereof.

A particularly preferred composition in which triglyceride blends of the invention may be used comprises 5-20 wt %, preferably 8 to 15 wt % DEFI (directly esterified fatty acid isethionate) and 5-15 wt % amphoteric, especially betaine.

A second component of the invention is the blend of saturated (hydrogenated); and unsaturated (non or partially hydrogenated) triglycerides. The blend typically comprises 1-40%, preferably 20-30% of the composition in which the blend is used.

According to the invention, the saturated (fully hydrogenated) triglyceride should comprise 15% to 35%, preferably 20 to 30% of the blend and unsaturated should comprise 85 to 65%, preferably 80 to 70% of blend. The blend should not contain more or less than the defined limit. If too many saturated triglycerides are used, applicants have found that this will depress the foam values relative to a blend which has only unsaturated oils. On the other hand, if too few saturated triglycerides are used, the composition will not have requisite rheology (spreadability) needed to allow the oil to deposit.

The critical amounts of saturated and unsaturated triglycerides may be characterized also by iodine value of the blend which defines the critical range. In the specific cases of soybean oil, for example, blends which have the required ranges of saturated to unsaturated oil (15 to 35% saturated and 85% to 65% unsaturated) have iodine value (IV), where IV is defined in the average measure of unsaturated bonds, of 81 to 120.

In addition, compositions of the invention may be defined by phase transition enthalpy (i.e., compounds or blends with similarly defined thermal property at the in-use temperature range have a comparable rheology and antifoaming effect). Thus, for example, if range of upper and lower limit of phase transition enthalpy of the blends of the invention is about the same as for petrolatum, the rheology of the blends and the petrolatum (relating to how they would be expected to deposit) would be about the same.

The "iodine value" (IV) represents the number of grams of iodine that an unsaturated compound or blend will absorb in a given time under arbitrary conditions. Low iodine value implies a high level of saturation (hydrogenation) degree, and visa versa. Iodine value can be determined by the WUJS method of the American Oil Chemists Society (AOCS Cd 1-25).

As noted above, when the vegetable oil is soybean oil, IV number of the blend should be above 70, preferably above 80, preferably 81 to 120, more preferably 90 to 110. These numbers reflect when the blends would have about 15-35 wt % saturated SBO and 85-65 wt % unsaturated SBO.

When the blend of the invention is used in compositions of the invention and when phase transition enthalpy (melting/cooling) is measured to fall within the defined criticality, the rheology of the composition will be such as to obtain optimal deposition. Specifically, compositions with the blend, when measured at a temperature range of −20 to 100° C., will have enthalpy of phase transition, measured in Joule/gram (J/g) of from 20 to 65, preferably 30 to 55. These enthalpy values represent a flattening of the peaks which indicate the composition will have ideal rheology for deposition.

Compositions of the invention are preferably aqueous based liquid cleanser compositions and contain, for example, at lest 30%, preferably at least 40% water. Measured using the protocol 3 as described in protocol section, the composition will have typically viscosities of between 10-1000 poise measured at 0.1 s$^{-1}$, preferably 100-500 poise.

In one embodiment, the personal wash composition comprising the oil blends of the invention (which have claimed saturate/unsaturated ratios) has a minimal amount or is substantially free of petrolatum. The composition has excellent oil deposition efficiency while maintaining good foaming property.

In a second embodiment, the invention provides a method of formulating liquid compositions comprising triglyceride blends which compositions deposit said triglycerides in an amount comparable to the amount of petrolatum which would be deposited from the same composition, and which compositions simultaneously have foaming value at least 70%, preferably at lest 75% as high than if the composition comprised unsaturated (non or partially hydrogenated) triglyceride.

This method comprises selecting about 1-40%, preferably 30% or less triglyceride blends wherein 15-35% of the blend comprises saturated (hydrogenated) triglyceride and 85-65% of the blend comprises unsaturated triglyceride, and formulating such blends into liquid compositions comprising said blends. A preferred composition is one comprising 5 to 25% DEFI and 5 to 15% amphoteric (e.g., betaine).

Protocol

1. Thermal Analysis

The phase transition profile of oil blends in this invention was characterized by Differential Scanning Calorimetry (DSC) using TA instruments Q-1000. Typically a 5-10 mg of oil blend was heated from room temperature up to 100° C. and cooled down to room temperature or lower at ramp rate of 3° C./minute. The phase transition energy was calculated by integrating the exotherm and endotherm curves using software Universal Analysis 2000 and averaged.

2. Lather Evaluation

Lather performance of personal wash samples and the antifoaming effect of containing oil blends have been evaluated by cylinder shaking method. In the method, a 5.0 ml of 5× diluted body wash samples was added into a 25.0 ml volumetric cylinder with cap. The foam was generated by hand shaking 10 times with same shaking speed and amplitude. The foam volume heights were read 20 seconds after shaking that allows the flash foam to be stabilized. The comparison of personal wash formulations with and without oil blends is used to illustrate the anti-foaming effect of oil blends.

3. Shear Viscosity Measurement

The shear viscosity of oil blends was measured by strain controlled rheometer from Rheometric Scientific ARES (SR-5, Rheometric Scientific, Piscataway, N.J.). The rheometer was set up with parallel plates 25 mm in diameter typically with 0.5 to 1.0 mm gaps between the top and bottom plates. Test temperature was at 23° C. Programmed steady shear rate sweeps were performed where the shear rates were logarithmically varied from 0.1 to 100 seconds$^{-1}$, with 5 points recorded per decade (i.e. per factor of ten increases in the shear rate). The output is viscosity as a function of shear rate.

EXAMPLES

Example 1

Thermal Transition of Blends

In order to show that there is significant difference in phase transition between a fully hydrogenated oil and the invention, for example, a system comprising mixture of 25% fully saturated (fully hydrogenated) soybean oil and 75% unsaturated soybean oil, applicants conducted differential scanning calorimetric studies (FIG. 1) on the two. As seen in FIG. 1, fully hydrogenated soybean oil (HSBO) has sharp phase transition peak (crystallization, measured in heat flow) with the maximum heat flow rate, for example, at about 2.6 watt/gram, and narrow distribution (measured in half peak temperature $\Delta T$) for example, about 3° C. By contrast, the mixture of 25% fully hydrogenated and 75% unsaturated oil yields significantly lowered (heat flow is less than 0.5 w/g) and broadened ($\Delta T$ is about 12° C.) phase transition peak.

Unexpectedly, the phase transition temperature of the said blend was shifted from about 48° C. to as low as 30° C. At body temperature (37° C.), which is higher than this crystal transition temperature, said blends quite unpredictably behave like petrolatum in liquid personal wash formulation. As indicated, this is a surprising and unpredictable mechanism relative to the art.

Figure 2:
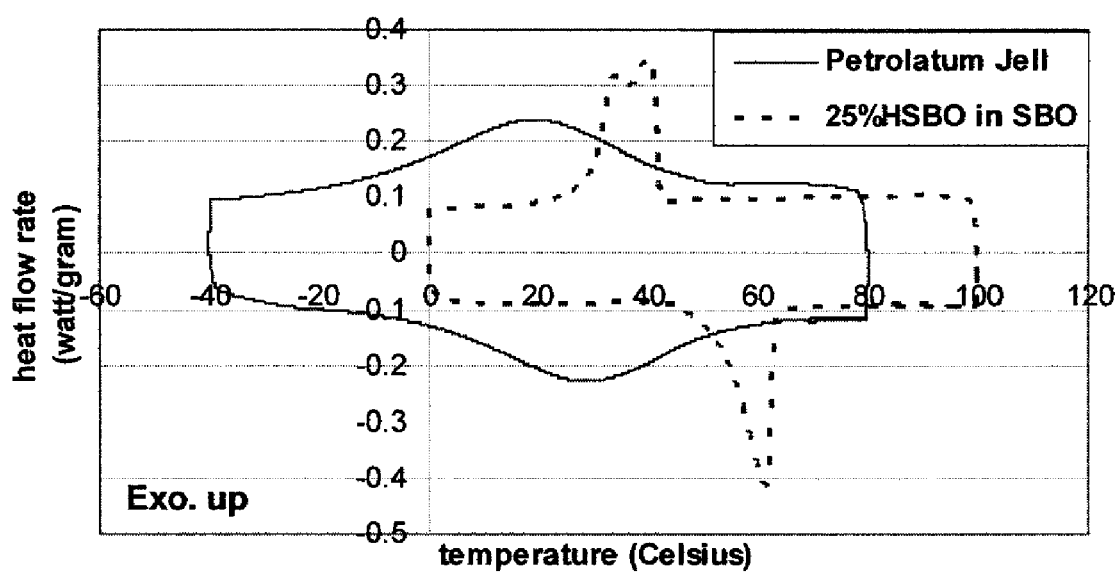
FIG. 2 is DSC measured phase transition cycle (heating and cooling) of the blend of FIG. 1 compared to petrolatum. As noted, the DSC phase transition of two has comparable amplitude of heat flow and overlapping temperature range which is why applicants believe these specific blends have rheology and surface morphology of drops analogous to that of petrolatum.
Figure 3:
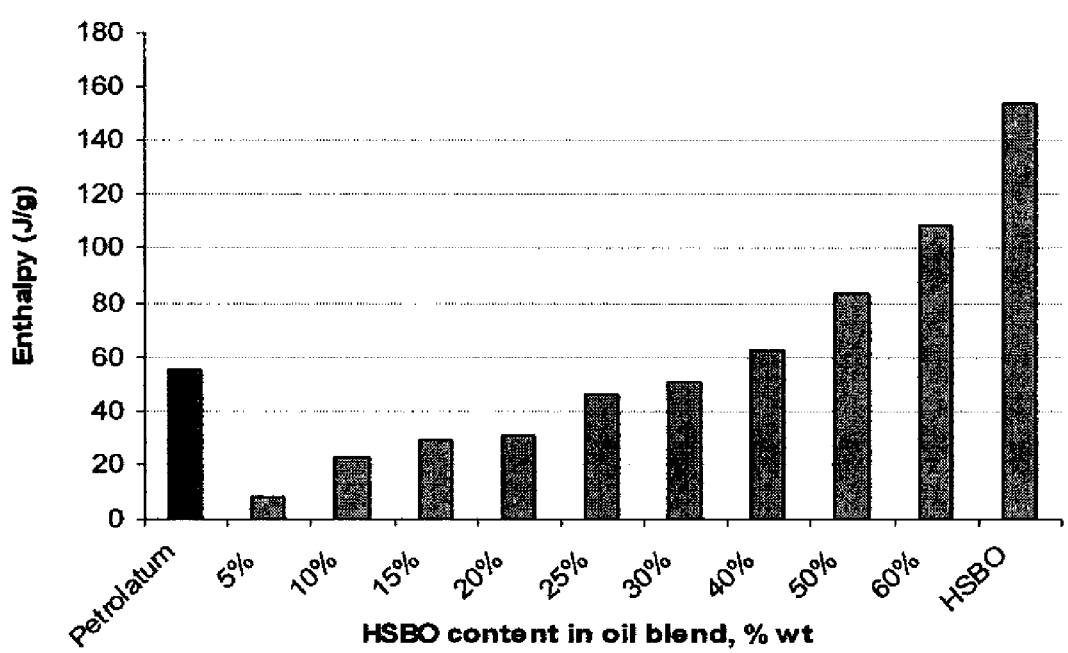
FIG. 3 is the crystallization enthalpies of partially hydrogenated soybean oil blends with varying compositions which could be used to identify the applicable ratio of fully hydrogenated soybean oil to its unsaturated counterpart that have thermal properties analogous to that of petrolatum.

To further indicate the significance of this lower, broadened and shifted phase transition peak, applicants also compared the heating/cooling cycle from the 25%/75% blend noted to the heat flow data of petrolatum. This comparison is seen in FIG. 2. As seen, the heat flow peaks for both are measured between 0.2 to 0.4 watts/g and the two are in the comparable range. More precisely, the phase transition energy, index by enthalpy, from heating and cooling cycles of the invention is comparable to petrolatum as seen in FIG. 3. Applicants believe these values explain why the specific blends of the invention have rheology and deposition substantially similar to that of petrolatum. That is, the blends now behave like petrolatum and yet, because this "structuring" involves only a mixing of defined ratio of oils as noted, there is no associated defoaming.

Example 2

Rheology of Blends

Another way to show that the rheology between petrolatum and the specific blends of the invention (e.g., blends wherein about 15 to 35%, preferably 20-30% of blend is fully saturated) is similar is to compare the shear profiles. This is done by plotting shear rate (measured in reciprocal seconds) versus viscosity (measured in Pascal-second) as shown in FIG. 4.

Figure 4:
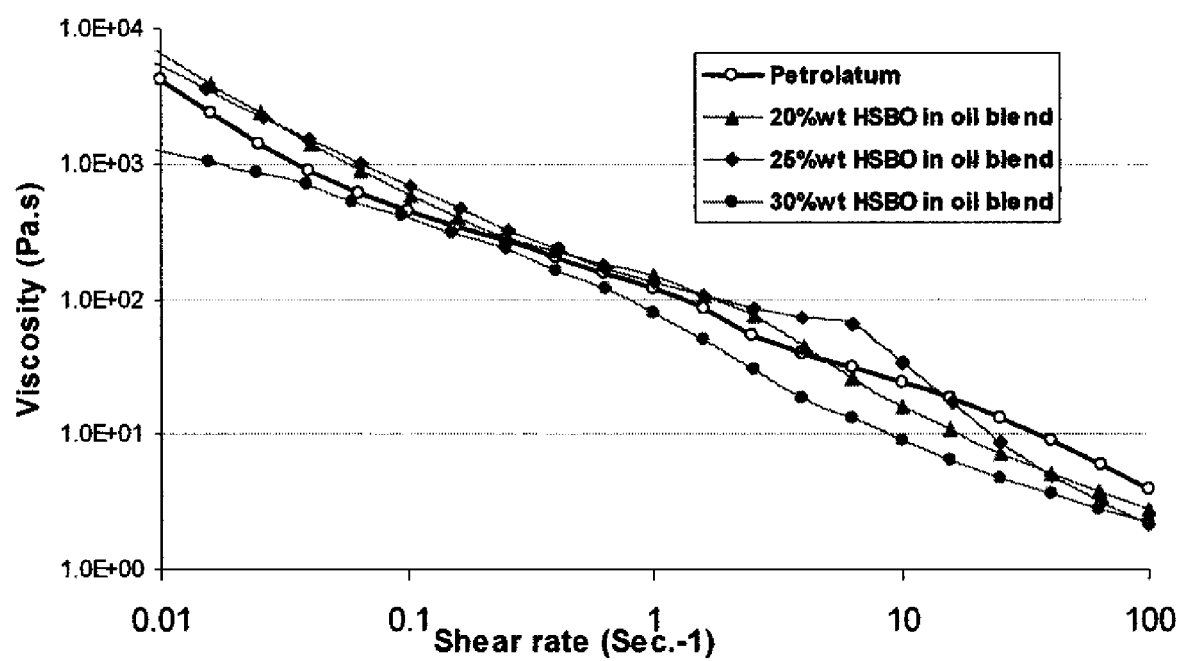
FIG. 4 is a plot of shear viscosity profile of the blends of invention compared to petrolatum. This again shows how profile is similar to that of petrolatum.

Once again, FIG. 4 shows that the viscosity for specific blends of the invention (i.e., with specific ratio of saturated to unsaturated triglyceride oil) has similar profile to that of petrolatum. This may also be important when using blends to meet possible requirements in liquid cleansing applications.

Example 3

Preparation of Blends

To achieve the blends having about 15-35% of blend being fully hydrogenated, it is possible, rather than using a controlled hydrogenation process starting from triglyceride oils (which hydrogenation may be difficult to control), to simply mix vegetable oil with fully hydrogenated vegetable fats (at temperature above melting point of either component) at a ratio required to yield the desired rheological and thermal properties.

Figure 5:
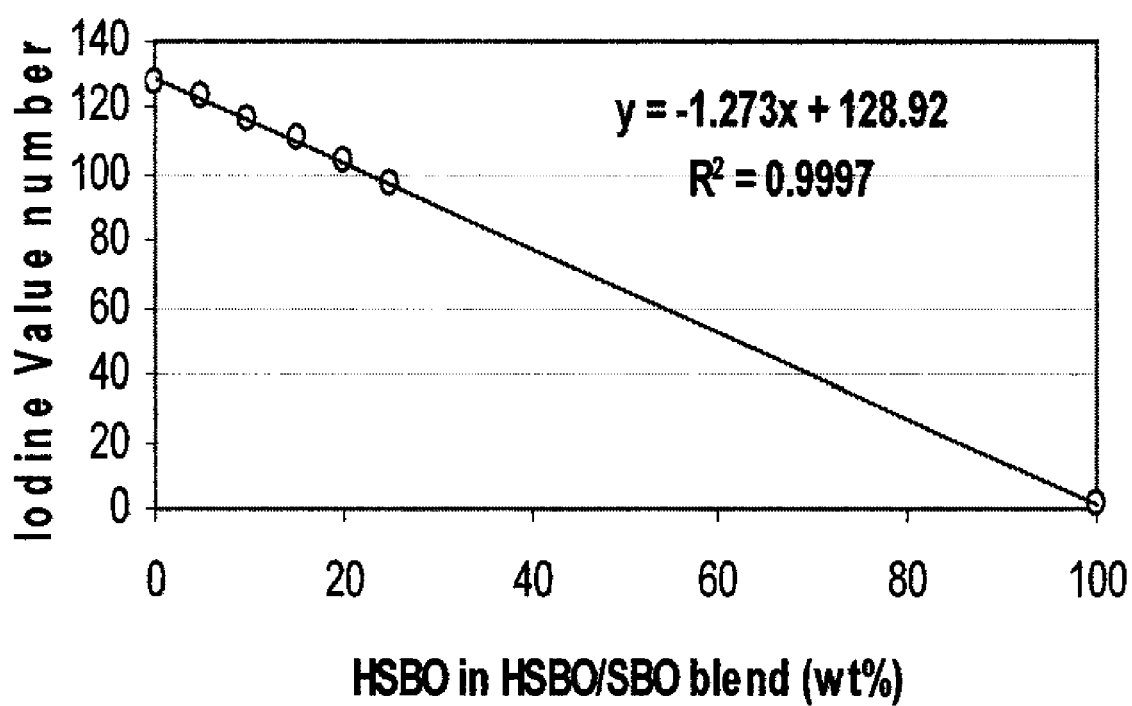
FIG. 5 is plot of linear correlation of iodine value (IV) of oil blends to content of hydrogenated oil in a blend (soybean oil, for example). In principle, other triglyceride based oils should also have this linearity with characteristic slopes and intercepts. It can be seen that preferred blends of the invention (comprising 15-35 wt % of blend of fully saturated HSBO) have IV number of 85-110. IV numbers outside this range (corresponding to ratios outside those of the invention) will not simultaneously meet rheology and foaming requirements of blends of the invention.

This, in turn, can be controlled by noting the strong linear correlation which applicants measured between iodine value (measure of lipid saturation) and the blend ratio of fully hydrogenated oils in the partially hydrogenated oil mixture. The measurement was conducted and plotted as seen in FIG. 5.

Specifically, from FIG. 5, it can be seen that, at level of blend comprising above 30% fully hydrogenated oil, the iodine value is below 91. Thus, by selecting blends where iodine value is above 81, preferably above 91, it is possible to select precisely the blends which will have the desired rheological and heat flow values required.

Example 4

Figure 6:
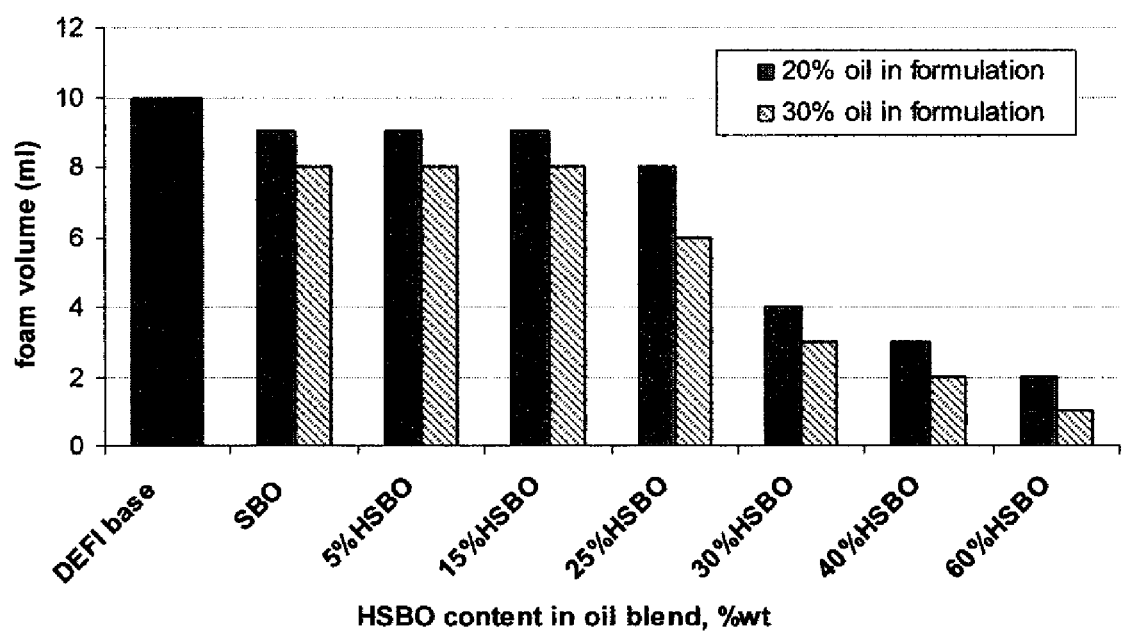
FIG. 6 is measure of foam volume of various triglyceride blends in a surfactant composition (composition comprising directly esterified fatty acyl isethionate as surfactant). The surfactant base (without emollient oil) was served as a control that gave the normalized foam volume of 10 ml. It is seen that, if there is too much fully saturated oil in the oil blend (e.g., >30 wt %), foam values are depressed. If there is not enough fully saturated oil, however, the oil blend will not have rheology of petrolatum and would not be expected to deposit as well as petrolatum.

As indicated, the blends of the invention are selected not only so that they will have rheology which will allow enhanced deposition, but also so that they will retain a foam volume at lest about 70% of the volume of compositions comprising unsaturated triglyceride oil (e.g., soybean oil). To show where foaming criticality lies, applicants proceeded as follows:

20% and 30% by weight of vegetable oils having varying amounts of saturated to unsaturated oils were formulated in DEFI liquid base (composition comprising directly esterified fatty acyl isethionate) and their lather performance was assessed by cylinder hand shaking method at room temperature. The foamability and the antifoaming effects from the structured oils could be compared from the foam volume as shown in FIG. 6. Clearly, the DEFI liquid composition containing 20% wt. or 30% wt. of partially hydrogenated soybean oils will not dramatically reduce the foam volume until the fully hydrogenated oils comprises >30% of the blend (i.e., when IV for soybean oil at least, falls below 91). That is, IV must be above 81, preferably below 105 until 91 when apparent antifoaming effect appears.

At lower oils content (<20%) in liquid composition, the applicable lower limit of IV number could be below 91 until 81 as noted because of proportionally lower antifoaming effect.

Example 5

The formulation below is a typical formulation in which triglyceride blend of the invention may be used.

| Formulation of DEFI liquid base | |
|---|---|
| Chemical Name | % in Product as 100% Active |
| Amount of Blend | 1-40%, preferably 5-35% |
| Long chain isethionates | 10-15 |
| Cocoamidopropyl Betaine | 8 |
| Lauric Acid | 2 |
| Cocoamide Monoethanolamine | 5 |
| Glycerin | 5 |
| Cationic Polymer | 0.1-0.5 |
| Starch | 1-3 |
| Petrolatum | 0-0.8 |

| -continued | |
|---|---|
| Formulation of DEFI liquid base | |
| Chemical Name | % in Product as 100% Active |
| Preservative | 0.1-0.2 |
| Perfume | 0.8 |
| Water | balance to 100 |

The invention claimed is:

1. A liquid personal product composition comprising:
   (a) 1 to 40% by wt. of surfactant system selected from anionic, nonionic, cationic, amphoteric/zwitterionic and mixtures thereof;
   (b) 1 to 40% by wt. of a blend of saturated and of unsaturated triglyceride oils, where said triglyceride oils comprise soybean oil, where the amount of saturated triglyceride is 15% to 35% of the blend and unsaturated is 85% to 65% of the blend and iodine value of said blend is 81 to 120;
   wherein when measured in a range of −20 to 100° C., the enthalpy of phase transition, measured in Joule/gram (J/g), of the blend is from 30 to 60; and
   wherein the foam value of composition comprising said blend is at least 70% of the value of the same composition where unsaturated triglyceride is used instead of said blend.

2. A composition according to claim 1 wherein the blend comprises 15 to 35% of the composition.

3. A composition according to claim 1, wherein amount of hydrogenated triglyceride is 20 to 30% of blend and unsaturated is 80 to 70% of the blend.

4. A composition according to claim 1, wherein the crystal phase transition enthalpy measured by differential scanning calorimetry is 30 to 60 Joule/gram.

5. A composition according to claim 1, wherein the blend comprises 1% wt to 40% wt of the composition and the composition comprises substantially no petrolatum.

6. A method for formulating compositions comprising triglyceride blends which compositions deposit said triglycerides in an amount comparable to the amount of petrolatum which would be deposited from the same composition, and which compositions simultaneously have foaming value at least 70% as high than if the composition comprised unsaturated (non or partially hydrogenated) triglyceride;
   wherein said method comprises (a) selecting triglyceride blends wherein 15-35% of the blend comprises saturated (hydrogenated) triglyceride and 65-85% of the blend comprises liquid triglyceride and measured iodine value of blend is 81 to 120, said triglyceride comprising soybean oil; and (b) formulating such blends and 1-40% by wt. of surfactant system selected from anionic, nonionic, cationic, amphoteric/zwitterionic and mixtures thereof into liquid compositions comprising said blends.

* * * * *